US012016529B2

(12) United States Patent
Pereira et al.

(10) Patent No.: US 12,016,529 B2
(45) Date of Patent: Jun. 25, 2024

(54) ENDOSCOPIC SCOPE DEVICE WITH A SENSOR

(71) Applicant: Boston Scientific Scimed, Inc., Maple Grove, MN (US)

(72) Inventors: Peter J. Pereira, Mendon, MA (US); Eric Wong, Framingham, MA (US); William Stanhope, Lunenburg, MA (US); Timothy Paul Harrah, Cambridge, MA (US); Thomas Michael Zappia, Jr., West Boylston, MA (US); Kimberly Degraaf, Holden, MA (US); Adam Perry Nodiff, Southborough, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 96 days.

(21) Appl. No.: 16/708,039

(22) Filed: Dec. 9, 2019

(65) Prior Publication Data

US 2020/0196839 A1 Jun. 25, 2020

Related U.S. Application Data

(60) Provisional application No. 62/782,511, filed on Dec. 20, 2018.

(51) Int. Cl.
*A61B 1/00* (2006.01)
*A61B 1/005* (2006.01)
(Continued)

(52) U.S. Cl.
CPC .......... *A61B 1/018* (2013.01); *A61B 1/00045* (2013.01); *A61B 1/00097* (2022.02);
(Continued)

(58) Field of Classification Search
CPC ............ A61B 1/00103; A61B 1/00009; A61B 1/00045; A61B 1/0051; A61B 1/045;
(Continued)

(56) References Cited

U.S. PATENT DOCUMENTS

| 4,901,735 A | * | 2/1990 | von Berg | ........... A61B 5/02156 |
| | | | | 600/561 |
| 5,067,491 A | * | 11/1991 | Taylor, II | .............. G01L 19/142 |
| | | | | 600/561 |

(Continued)

FOREIGN PATENT DOCUMENTS

| CN | 206566332 U | 10/2017 |
| CN | 107440672 | 12/2017 |

OTHER PUBLICATIONS

Office Action in Chinese Application No. 201980085108.6, dated Jan. 25, 2024 (14 pages).

*Primary Examiner* — Timothy J Neal
(74) *Attorney, Agent, or Firm* — Bookoff McAndrews, PLLC

(57) ABSTRACT

A scope system includes a processor and a scope device. The scope device includes a handle configured to remain outside of the body and an elongated shaft extending from the handle to a distal tip and including a working channel extending therethrough. The working channel is open at the distal tip of the shaft. The shaft is inserted through a bodily lumen to a target surgical site. The shaft includes at least one sensor transmitting to the processor sensor data relating to the target surgical site.

19 Claims, 4 Drawing Sheets

(51) Int. Cl.
  *A61B 1/018* (2006.01)
  *A61B 1/045* (2006.01)
(52) U.S. Cl.
  CPC ........ *A61B 1/00103* (2013.01); *A61B 1/0051* (2013.01); *A61B 1/045* (2013.01); *A61B 2562/0219* (2013.01); *A61B 2562/0247* (2013.01); *A61B 2562/0257* (2013.01); *A61B 2562/0271* (2013.01)
(58) Field of Classification Search
  CPC .... A61B 2562/0219; A61B 2562/0247; A61B 2562/0257; A61B 2562/0271; A61B 5/6847; A61B 1/307; A61B 1/00071; A61B 1/0008; A61B 1/018; A61B 5/033; A61B 5/035; A61B 5/036; A61B 2562/02; A61B 2562/0214
  See application file for complete search history.

(56) References Cited

U.S. PATENT DOCUMENTS

| | | | | |
|---|---|---|---|---|
| 5,715,827 | A * | 2/1998 | Corl | G01L 19/147 600/561 |
| 5,902,248 | A * | 5/1999 | Millar | A61B 8/12 600/561 |
| 6,398,738 | B1 * | 6/2002 | Millar | A61B 5/6853 600/486 |
| 2005/0080342 | A1 * | 4/2005 | Gilreath | A61B 1/05 600/476 |
| 2006/0069306 | A1 * | 3/2006 | Banik | A61B 1/000095 600/117 |
| 2006/0211944 | A1 * | 9/2006 | Mauge | A61B 5/031 600/488 |
| 2009/0318757 | A1 * | 12/2009 | Singh | A61J 15/0026 600/109 |
| 2010/0010328 | A1 * | 1/2010 | Nguyen | A61B 5/0215 600/364 |
| 2010/0100010 | A1 * | 4/2010 | Andarawis | A61B 5/0028 600/587 |
| 2014/0128823 | A1 * | 5/2014 | Odland | A61B 5/15003 604/319 |
| 2014/0167190 | A1 * | 6/2014 | Hodgson | B81C 3/005 438/51 |
| 2014/0180028 | A1 * | 6/2014 | Burkett | A61B 5/02152 600/585 |
| 2014/0180142 | A1 * | 6/2014 | Millett | A61B 5/0215 600/488 |
| 2014/0243703 | A1 * | 8/2014 | Schmidt | A61B 5/031 600/561 |
| 2014/0275950 | A1 * | 9/2014 | Hoseit | A61B 5/6851 600/407 |
| 2014/0276138 | A1 * | 9/2014 | Millett | A61B 5/6851 600/585 |
| 2015/0073217 | A1 | 3/2015 | Powell et al. | |
| 2015/0099926 | A1 * | 4/2015 | Davidson | A61B 1/04 600/103 |
| 2015/0265167 | A1 * | 9/2015 | McGowan | A61B 5/0084 600/478 |
| 2015/0313478 | A1 * | 11/2015 | Veszelei | A61B 5/02158 600/483 |
| 2015/0319410 | A1 * | 11/2015 | Gu | G01N 21/954 348/82 |
| 2016/0183819 | A1 * | 6/2016 | Burnett | A61B 5/14507 600/309 |
| 2017/0055811 | A1 * | 3/2017 | Germain | A61B 1/00135 |
| 2017/0055908 | A1 * | 3/2017 | Radman | A61B 5/0084 |
| 2017/0079508 | A1 * | 3/2017 | Ikeda | A61B 1/00006 |
| 2017/0119474 | A1 | 5/2017 | Kronman | |
| 2017/0164867 | A1 * | 6/2017 | Kassab | A61B 5/0215 |
| 2018/0132703 | A1 * | 5/2018 | Reever | A61B 1/05 |
| 2018/0153381 | A1 * | 6/2018 | Wei | A61B 1/00002 |
| 2018/0228553 | A1 * | 8/2018 | Bai | A61B 34/30 |
| 2019/0290207 | A1 * | 9/2019 | Wright | A61L 29/14 |
| 2019/0298321 | A1 * | 10/2019 | Intintoli | A61B 1/07 |
| 2020/0015670 | A1 * | 1/2020 | Mullick | A61B 5/14507 |

* cited by examiner

ENDOSCOPIC SCOPE DEVICE WITH A SENSOR

PRIORITY CLAIM

The present disclosure claims priority to U.S. Provisional Patent Application Ser. No. 62/782,511 filed Dec. 20, 2018; the disclosure of which is incorporated herewith by reference.

FIELD

Aspects of the present disclosure relate generally to medical devices and methods. Particular aspects relate generally to endoscopic devices and methods.

BACKGROUND

Flexible ureteroscopes utilized in kidney stone removal are typically re-usable. As such, the materials and the design are generally robust enough for multiple uses and multiple disinfections. Manufactures have at times avoided adding sensors that might provide physicians with valuable data because these sensors are typically not robust enough to withstand multiple uses and disinfections. In some instances, the sensors may break or malfunction or go out of calibration.

SUMMARY

The present disclosure is directed to a scope system, comprising a processor and a scope device. The scope device comprises a handle configured to remain outside of the body and an elongated shaft extending from the handle to a distal tip and including a working channel extending therethrough, the working channel being open at the distal tip of the shaft, the shaft being configured to be inserted through a bodily lumen to a target surgical site, the shaft including at least one sensor transmitting to the processor sensor data relating to the target surgical site.

In an embodiment, the scope device may be a single-use scope device.

In an embodiment, the sensor may be a chip pressure sensor, the chip pressure sensor including an active portion which measures a pressure exerted by the target surgical site on the chip pressure sensor, the chip pressure sensor providing pressure data to the processor via a lead coupled thereto.

In an embodiment, the sensor may be a fiber optic pressure sensor extending through the length of the shaft, a distal end of the fiber optic pressure sensor being positioned at a distal surface of the distal tip and providing to the processor a pressure readout from the distal tip.

In an embodiment, the sensor may be a temperature sensor positioned at the distal surface of the distal tip and providing a temperature readout from the distal tip to the processor.

In an embodiment, the sensor may be a capacitive sensor configured to measure external forces exerted on tissue by the shaft, the capacitive sensor being positioned on an outer circumference of the shaft and including a wire that extends through the shaft to connect to the processor.

In an embodiment, the scope device may include a series of capacitive sensors placed along a length of the shaft, the capacitive sensors measuring a ureteral peristalsis wave force.

In an embodiment, the system may further comprise a fluid source coupled to the scope device, the fluid source providing fluid through the shaft to the target surgical site.

In an embodiment, the processor may include a display screen and a user interface, the display screen displaying sensor data to the user.

In an embodiment, the sensor may be a gyroscope sensor to measure an angular rate of the elongated shaft as it deflects within the target cavity.

In an embodiment, the sensor may be a pH sensor.

The present disclosure is directed to a scope system, comprising a processor and a single-use scope device. The scope device including a handle configured to remain outside of the body and an elongated shaft extending from the handle to a distal tip and including a working channel extending therethrough, the working channel being open at the distal tip of the shaft, the shaft being configured to be inserted through a bodily lumen to a target surgical site, the shaft including first and second sensors transmitting to the processor first and second sensor data, respectively.

In an embodiment, one of the first and second sensors may be one of a pressure sensor, a temperature sensor, a pH sensor, a capacitive sensor and a gyroscope sensor.

In an embodiment, the system may further comprise a fluid source coupled to the scope device, the fluid source providing fluid through the shaft to the target surgical site.

In an embodiment, the processor may include a display screen and a user interface, the display screen displaying the first and second sensor data to the user.

BRIEF DESCRIPTION

DETAILED DESCRIPTION

Figure 1:
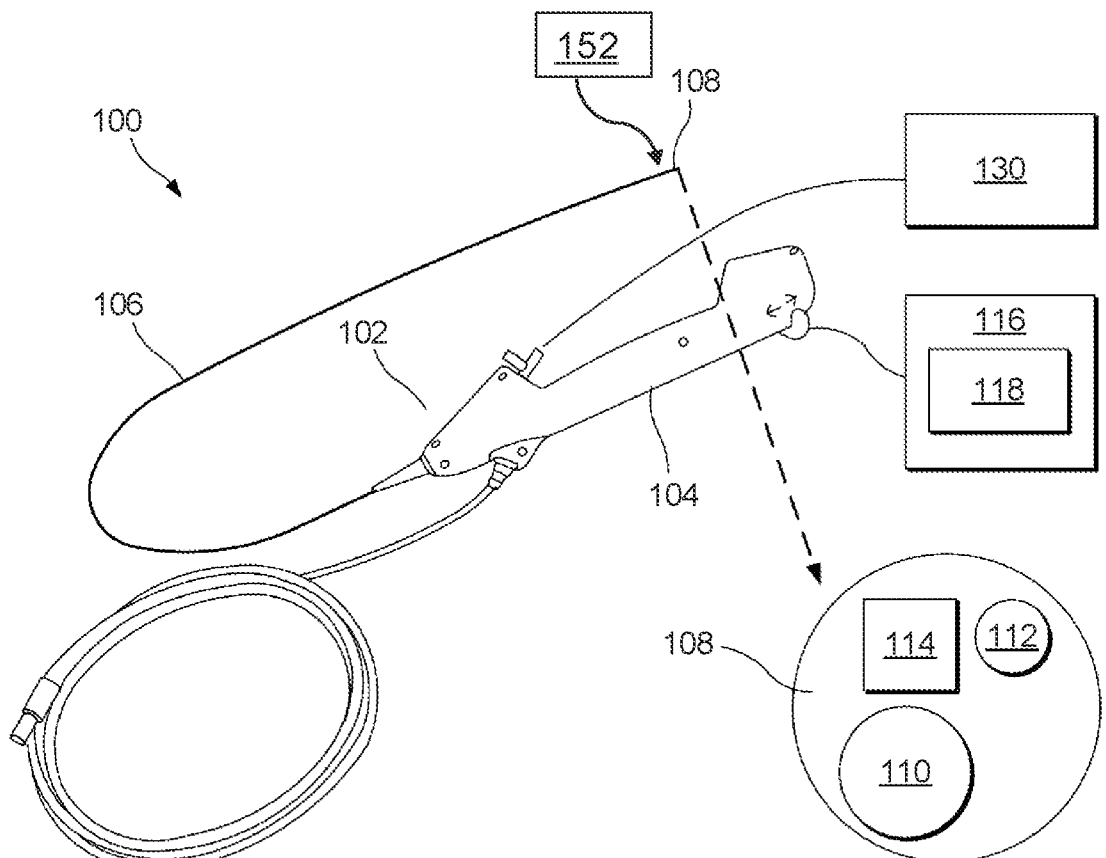
FIG. 1 shows a schematic view of a scope system according to an exemplary embodiment of the present disclosure.

The present invention may be understood with respect to the following description and the appended drawings, wherein like elements are referred to with the same reference numerals. The present invention relates to scope devices and methods which incorporate sensors for providing feedback data to a physician during a procedure. Exemplary embodiments describe a scope device such as, for example, a single-use flexible ureteroscope, such as the LithoVue™ scope device, including a lumen or shaft which incorporates sensors therein to provide user feedback during the single use. Exemplary sensors include pressure sensors, temperature sensors, capacitive sensors, absorption spectroscopy sensors, pH sensors, and/or gyroscope sensors. It should be noted that the terms "proximal" and "distal" as used herein are intended to refer to a direction toward (proximal) and away from (distal) a user of the device.

In an exemplary embodiment depicted in FIG. 1, a scope system 100 comprises a scope device 102. The scope device 102 may be any single-use scope device configured for use in minimally invasive procedures such as a ureteroscope, for example, under the brand name LithoVue™, an endoscope, a hysteroscope, a bronchoscope, a cystoscope, or any other similar device. The scope device 102 comprises a handle 104 which, during use, remains outside a living body, and a shaft 106 size and shaped to be inserted through a body lumen to a target cavity. The shaft 106 extends from a proximal end coupled to the handle 104 to the distal tip 108 and includes a working channel 110 extending therethrough. The handle 104 includes an actuation mechanism which allows the user to control and articulate the shaft 106 when navigating the body lumen. In an exemplary embodiment, the scope device 102 includes means of illuminating and visualizing the body lumen and any inner cavities.

For example, the scope device 102, in this embodiment, includes a camera 114 and a light source 112, shown in FIG. 1. The camera 114 and light source 112 may be controlled manually via buttons (or other similar mechanisms) on either the handle 104 or on a processing device 116, as will be described in further detail below and as would be understood by those skilled in the art. In an exemplary embodiment, the scope device 102 also includes at least one sensor incorporated therein, as will be described below. The sensor, in some embodiments, is positioned at the distal tip 108 of the shaft 106. In other embodiments, the sensor may be positioned on a portion of the outer surface of the shaft 106. In an exemplary embodiment, the scope device 102 is connected to a fluid source 130 via, for example, a supply line. The fluid source 130 provide fluid flow through the supply line, the handle 104 and the shaft 106 to the target body cavity. Specifically, the shaft 106 provides a fluid path to deliver, for example, irrigation fluid to the target lumen or cavity.

The scope system 100 also comprises a processing device 116 such as, for example, a computer. The processing device 116 is capable of performing various functions such as calculation, control, computation, display, etc. The processing device 116 is also capable of tracking and storing data pertaining to the operations of the scope system 100 and each component thereof. In an exemplary embodiment, the processing device 116 includes network communication capabilities, such as Wi-Fi, through which the device may be connected to, for example, a social area network. The processing device 116 may also receive signals from the sensors and modular components (i.e., the fluid source 130) of the scope system 100. In an embodiment, the main processing 116 may communicate with a database for "best practice" suggestions and the maintenance of patient records which may be displayed to the user on a display screen 118. The display screen 118 may be configured to show feedback related to sensors incorporated into the scope system 100. For example, the display screen 118 provides the user with a live video feed 120 of the target tissue/vessel/cavity from the camera 114 positioned on the distal tip 108 of the scope device 102, as shown in FIG. 3.

The processing device 116 and/or the display screen 118 may include one or more user interface components such as buttons, switches, knobs or a touch screen interface. A touch screen interface may include the display screen 118 and may include switches or knobs in addition to touch capabilities. The user interface allows the user to input/adjust various functions of the scope system 100 such as, for example, pressure, temperature, etc. The user may also configure parameters and alarms (such as max pressure alarm), information to be displayed and the procedure mode. The user interface may also allow the user to add, change or discontinue the use of various sensors within the scope system 100.

Figure 2:
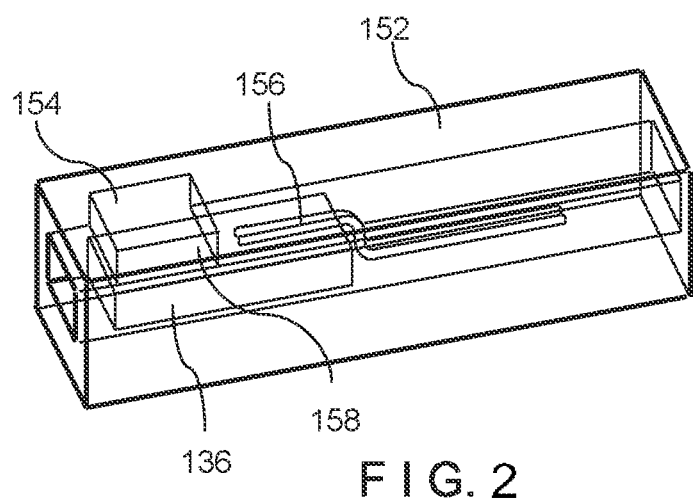
FIG. 2 shows a perspective view of a pressure sensor of the scope device of the scope system of FIG. 1 according to a first exemplary embodiment of the present disclosure.
Figure 3:
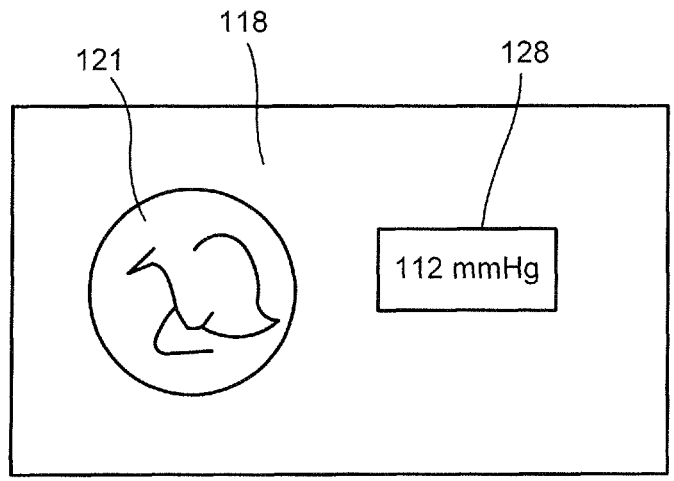
FIG. 3 shows an exemplary display screen with a pressure reading from the pressure sensor of FIG. 2.
Figure 4:
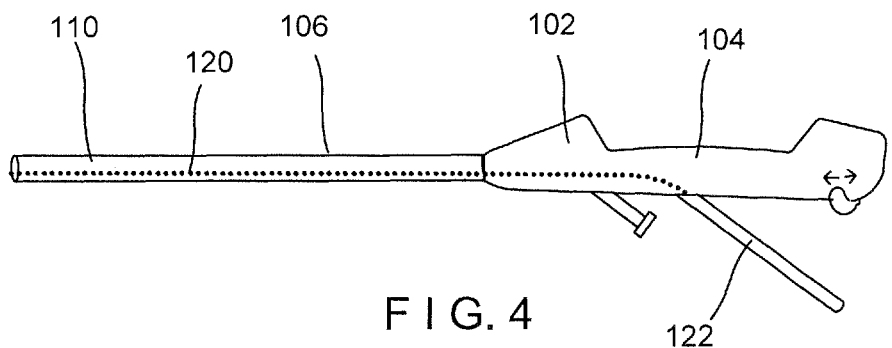
FIG. 4 shows a side view of a scope device of the scope system of FIG. 1 according to a second exemplary embodiment of the present disclosure.

In an exemplary embodiment, the scope device 102 includes a pressure sensor 136, as shown in FIGS. 2-4. The pressure sensor 136, in this embodiment, is positioned at the distal tip 108 of the scope device 102 and provides to the physician numerical measurements of, for example, intrarenal pressure via the display screen. As would be understood by those skilled in the art, rapidly rising intrarenal pressures may increase the risk of extravasation with the potential to cause pyelosinus, pyelovenous, and/or pyelolymphatic backflow of an irrigant provided to the kidney. High intraluminal pressure, in some instances, may make it easier for bacteria and endotoxins to be absorbed into the blood, possibly resulting in postoperative fever. High pressure may also cause lymph node and venous reflux which may lease to fluid leakage, post-operative pain, urosepsis and renal injury. Thus, a pressure sensor 136 added to the scope device 102 may limit the occurrence of such eventualities.

As shown in FIG. 2, the pressure sensor 136 may be a chip sensor sized and shaped to be positioned within or on a wall of the shaft 106 at the distal tip 108 of the scope device 102. The chip sensor 136, in the embodiment of FIG. 2, may be embedded in a larger housing 152 which aids in mounting the chip sensor 136 within the shaft 106. However, in other embodiments, the chip sensor 136 may be mounted directly into the shaft 106, as would be understood by those skilled in the art. Rather, the chip sensor 136 may be mounted in a cavity, pocket or other feature within the distal tip 108 of the scope device 102. This feature provides a base for mounting of the chip sensor 136 while allowing access to the medium to be measure to the active portion of the sensor. In the present embodiment, the housing 152 includes a window or port 154 which allows the medium being measured to come into contact and exert pressure on the membrane or active area 158 of the chip sensor 136. This pressure is translated into an electrical signal which is transmitted to the processing device 116.

The window 154 allows for a water tight coating to be applied while allowing the chip sensor 136 to measure the pressure exerted thereon and protects a lead 156 extending from the chip sensor 136 from stress that could break the electrical contact. As shown in the figure, the lead 156 extends from the chip sensor 136 through the shaft 106 and is coupled to, for example, signal conditioning circuitry. The chip sensor 136 is positioned in the distal tip 108 of the scope device 102 relatively close to a surface of the diameter of the shaft 106. In some embodiments, the chip sensor 136 may be positioned at the external surface. In other embodiments, the chip sensor 136 may be positioned slightly below the surface so long as the medium is able to contact the active area 158 of the chip sensor 136. The chip sensor 136 may provide a pressure readout 128 from the scope device 102 to the display screen 118 of the processing device 116. In an embodiment, the display screen 118 may display the actual pressure in real time. The physician may then manually adjust the irrigation of the body cavity as required if intrarenal pressures are too high. Furthermore, as previously noted, the physician may input a "max" pressure into the processing device 116 which triggers an alarm or an alert on the display screen if reached by the readout of the chip sensor 136.

Figure 5:
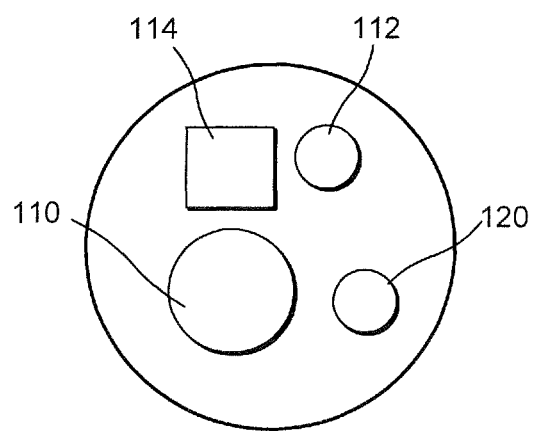
FIG. 5 shows a front view of the shaft of the scope device of FIG. 4.

In another exemplary embodiment, depicted in FIGS. 4-5, the scope device 102 includes a fiber optic pressure sensor 120. In this embodiment, the pressure sensor 120 extends through the shaft of the scope with a distal end 122 thereof positioned at a distal surface 124 of the distal tip 108, as shown in FIG. 4. The pressure sensor 120 in this embodiment is connected at a proximal end to the processing device 116 or any other processing device that is either directly or indirectly connected to the processing device 116. The pressure sensor 120 may extend through the working channel 110 or another separate lumen extending through the length of the shaft 106. As shown in FIG. 4, the handle 104 may include a hub or connection port 122 through which the pressure sensor 120 may extend to connect to the processing device 116. As with the pressure sensor 136, the pressure sensor 120 may provide a pressure readout 128 from the scope device 102 to the display screen 118 of the processing device 116. In an embodiment, the display screen 118 may display the actual pressure in real time. The physician may the manually adjust the irrigation of the body cavity as required if intrarenal pressures are too high. Furthermore, as previously noted, the physician may input a "max" pressure into the processing device 116 which triggers an alarm or an alert on the display screen if reached by the readout of the pressure sensor 120.

Figure 6:
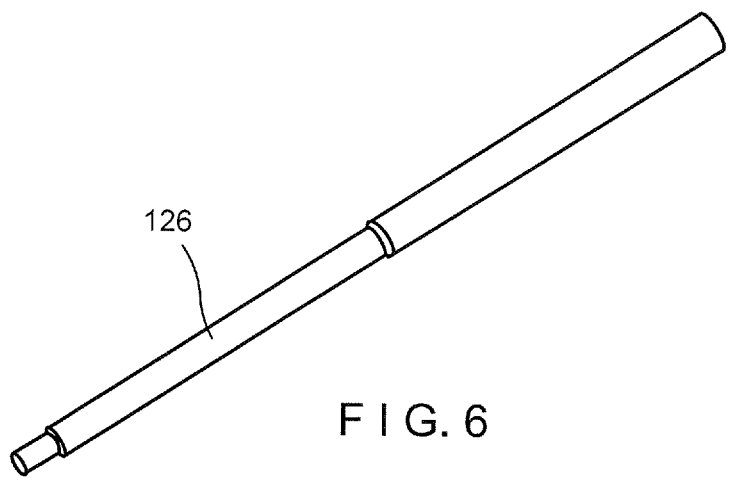
FIG. 6 shows a perspective view of a temperature sensor according to an exemplary embodiment of the present disclosure.

In another exemplary embodiment, depicted in FIG. 6, the scope device 102 includes a temperature sensor 126. The temperature sensor 126 may be beneficial during, for example, lithotripsy procedures in which a laser is used within the target body cavity. In such procedures, if there is insufficient irrigation, the temperature within the body cavity may rise to unsafe levels. A temperature sensor at the distal tip 108 of the shaft 106 of the scope device 102 allows the user to more closely monitor the environment of the body cavity into which the distal tip 108 has been inserted, providing feedback to the physician via the display screen 118.

Figure 7:
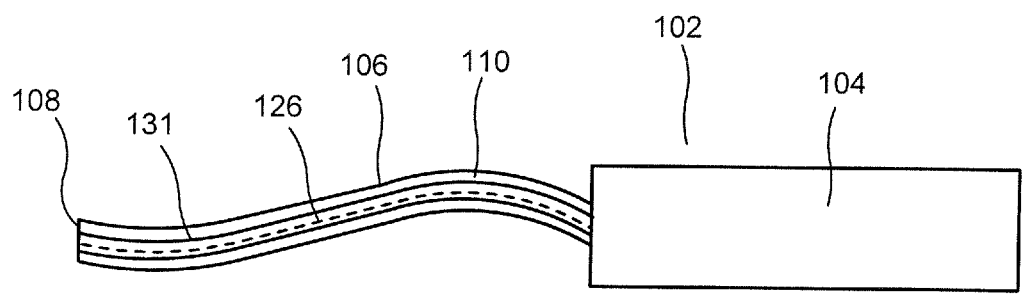
FIG. 7 shows a side view of a scope device including a temperature sensor according to an exemplary embodiment of the present disclosure.

The temperature sensor 126 may be any suitable temperature sensors such as, for example, a thermocouple, thermistor (resistant temperature device), or fiberoptic temperature sensor. In the present embodiment, a micro thermocouple is depicted. The temperature sensor 126 may be an elongated sensor (as shown in FIGS. 6-7) that extends through the length of the shaft 106 with a distal end thereof integrated into the distal tip 108 of the shaft 106. The temperature sensor 126, in this embodiment, extends through a lumen 131 separate from the working channel 110 and is connected at a proximal end to leads connected to signal conditioning circuitry. The temperature readout may be displayed on the display screen 118 numerically, in color coded indications or in any other graphic display. For example, the color green may indicate normal operating temperatures while yellow indicates above-normal temperatures and the color red indicates dangerous temperatures. As with the pressure sensors 136, 120, the processing device 116 may be configured to display an alert or an alarm when the temperature readout reaches dangerous temperatures or, for example, when the rate of change of the temperature indicates a potentially unsafe condition.

Figure 8:
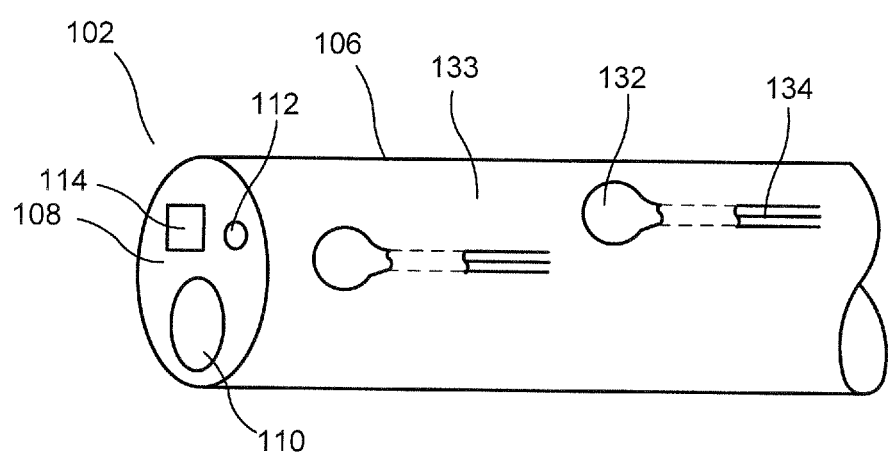
FIG. 8 shows a perspective view of a shaft of a scope device according to an exemplary embodiment of the present disclosure.

In another exemplary embodiment, depicted in FIG. 8, the scope device 102 includes at least one capacitive sensor 132. In some instances, the insertion of the shaft 106 into the body lumen/cavity and the deflection of the distal tip 108 of the shaft 106 in the lumen/cavity may exert a large force on the walls of the lumen within which the scope device 102 is inserted possibly damaging the tissue and/or causing pain. Adding a capacitive-based force sensor 132 to the scope device 102 that can accurately, and with high repeatability, measure forces of the shaft 106 exerts on the surrounding tissue may help minimize such trauma. In this embodiment, one or more capacitive sensors 132 may be positioned on an outer surface 133 of the shaft 106.

In FIG. 8, two capacitive sensors 132 are shown, however, this number is only exemplary. The capacitive sensors 132 are positioned at a distal portion of the shaft 106 to measure force exerted radially outward against the surrounding tissue as the distal tip 108 deflects. However, it will be understood by those skilled in the art that the capacitive sensors 132 may be positioned anywhere along the length of the shaft 106 to measure force exerted against which the various parts of the scope device 102 are pushing. Each of the capacitive sensors 132 may be connected to a wire 134 that extends the length of the shaft 106 to connect to, for example, the processing device 116. Each of the capacitive sensors 132 would have its own lead connected to signal conditioning circuitry.

The wires 134 may extend through a lumen separate from the working channel 110 or may be embedded in the wall of the shaft 106 as would be understood by those skilled in the art. The measured force applied against the surrounding tissue by the shaft 106 may then be displayed on the display screen 118. Thus, the physician can act accordingly if too much force is being applied. In addition, in an exemplary embodiment, if a series of capacitive sensors 132 are placed along the length of the scope device 102, ureteral peristalsis wave force can be measured, which may indicate the health of the ureter from a diagnostic standpoint.

In another exemplary embodiment, the scope device 102 includes a pH sensor 144 which allows the physician to identify kidney stone types based on the pH. For example, a low urine pH may be identified as a precursor for a uric acid kidney stone. The two major factors that promote uric acid precipitation are a high urine uric acid concentration and the acid urine pH, which drives the reaction, $H^+ + Urate^- \leftrightarrow$ Uric acid, to the right, converting the relatively soluble urate salt into insoluble uric acid. A low urine pH is the more significant of these two biochemical risk factors for the development of uric acid nephrolithiasis. Uric acid solubility in the urine falls from approximately 200 mg/dL (1.2 mmol/L) at a urine pH of 7 (a setting in which 95 percent of uric acid is present as the more soluble urate anion) to 15 mg/dL (0.09 mmol/L) at a urine pH of 5 (a setting in which most of the uric acid is less soluble, undissociated acid). Thus, with the pH sensor 144, the physician is capable of monitoring the pH of the urine so as to identify the type of tissue or stone that is present within the body cavity.

Figure 9:
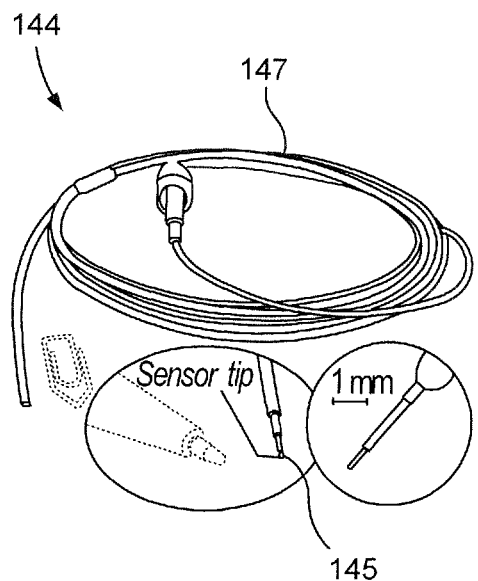
FIG. 9 shows a perspective view of a fiber optic pH sensor according to an exemplary embodiment of the present disclosure.

FIG. 9 depicts a fiber optic pH sensor 144 that may be integrated into the shaft 106 of the scope device 102. The sensor tip 145 is positioned at the distal end 108 of the shaft 106 so as to have easy access to the target tissue. A cable or wire 147 of the fiber optic pH sensor 144 extends through shaft 106, either within the working channel 110 or a separate lumen, and is connected to signal conditioning circuitry. In an exemplary embodiment, the fiber optic pH sensor 144 is approximately 1 mm in diameter so as to easily fit within the shaft 106 of the scope device 102. The measured pH is displayed on the display screen 118 so as to be visible by the physician.

Figure 10:
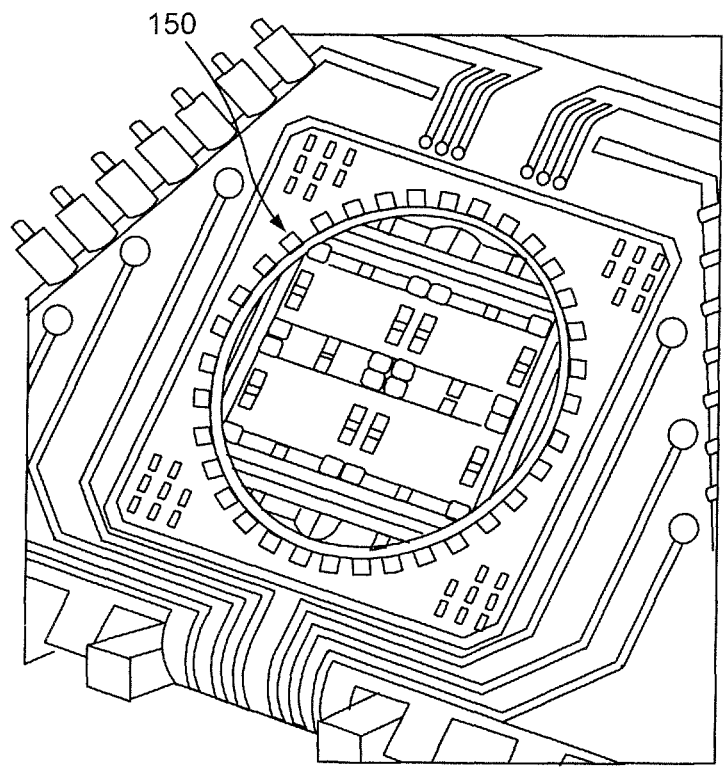
FIG. 10 shows a perspective view of a gyroscope sensor according to an exemplary embodiment of the present disclosure.

The scope device 102, according to another exemplary embodiment, includes a gyroscope sensor 150. An exemplary gyroscope sensor is depicted in FIG. 10. The gyroscope sensor 150 may be incorporated into the distal tip 108 of the shaft 106 to measure angular rate or angular velocity of the shaft 106 as it deflects or moves within the target cavity. The gyroscope sensor 150 is used to maintain the orientation of the distal end 108 and, for example, the video feed provided by the camera 114. Thus, the physician is able to know what position the distal tip 108 of the scope device 102 is moving as he or she investigates the target lumen/cavity. The gyroscope sensor 150 may be approximately 1 mm by 1 mm in size, or smaller, and positioned on the distal tip 108 of the shaft 106. The gyroscope is there to help with orientation of the distal tip 108 as it relates to the image produced by the camera. It can also be used as part of an inertial navigation system which would help the physician in determining the position of the distal tip 108 in the collection system (bladder, urethra, kidney).

It is noted that although the described embodiments only incorporate a single sensor into the shaft 106 of the scope device 102, any number and combination of any of the sensors described above may be included in a single scope device 102. For example, the distal tip 108 of the shaft 106 may include one, two or more sensors positioned thereon. Additionally, the sensors may be positioned anywhere along the shaft 106, not just on the distal tip 108 or a distal portion of the shaft 106.

An exemplary method of use of the scope system 100 includes inserting the distal tip 108 of the shaft 106 into a target body lumen (e.g., via a naturally occurring bodily orifice) such as the urethra and advancing the shaft 106 therethrough to a target cavity within, for example, the kidney. In some embodiments, irrigation fluid may be provided through the working channel 110 of the shaft 106 and into the target lumen. Once the shaft 106 has been positioned at a target location in the kidney as desired, sensors such as the pressure sensors 120, 136, the temperature sensor 126, the capacitive sensor 132, the pH sensor 144 and the gyroscope sensor 150, along with the camera 114 provide feedback to the user and/or processing device 116 regarding the conditions of the target anatomy in which the scope device 102 is positioned, which may be displayed on the display screen 118. Simultaneously, the user and/or the entire surgical team may be alerted if specific conditions exceed or fall below pre-entered thresholds via an audio or visual alert. Manual adjustment may occur through buttons or dials on the processing unit 116 or through touch buttons on the display screen 118 if a touch-display is used.

It will be appreciated by those skilled in the art that the current devices and methods are not limited to the disclosed embodiments. For example, the disclosed debris removal system 100 may be used in various other procedures such as, for example, hysteroscopies, cystoscopies, etc. Thus, the system 100 is not limited to use with a ureteroscope but may be used with other devices such as cystoscopes, hysteroscopes or any other device with a shaft inserted into a body channel/lumen/cavity.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A scope system, comprising:
a processor; and
a single-use scope device, comprising:
a handle configured to remain outside of a body; and
an elongated shaft extending from the handle to a distal tip and including a working channel extending therethrough, the working channel being open at the distal tip of the shaft and adjacent to a camera and a light source, the shaft being configured to be inserted through a bodily lumen to a target surgical site, the shaft including a pressure sensor embedded in a housing mounted within the distal tip of the shaft, the pressure sensor being configured to measure intraluminal pressure relating to a target surgical site and to transmit to the processor sensor data relating to the target surgical site, an active portion of the pressure sensor being adjacent a window of the housing and proximate a surface of a diameter of the shaft, wherein the active portion is covered by a water-tight coating within the window that separates the active portion of the pressure sensor from fluid surrounding the scope device while permitting the active portion of the pressure sensor to measure pressure in the fluid surrounding the scope device.

2. The system of claim 1, wherein the pressure sensor is a chip pressure sensor which measures a pressure exerted by the target surgical site on the chip pressure sensor.

3. The system of claim 1, wherein the scope device further includes a temperature sensor positioned at a distal surface of the distal tip and providing a temperature readout from the distal tip to the processor.

4. The system of claim 1, wherein the scope device further includes a force sensor configured to measure external forces exerted on tissue by the shaft, the force sensor being positioned on an outer circumference of the shaft and including a wire that extends through the shaft to connect to the processor.

5. The system of claim 1, wherein the scope device includes a series of force sensors placed along a length of the shaft, the force sensors measuring a ureteral peristalsis wave force.

6. The system of claim 1, further comprising a fluid source coupled to the scope device, the fluid source providing fluid through the shaft to the target surgical site.

7. The system of claim 1, wherein the processor includes a display screen and a user interface, the display screen displaying the sensor data to a user, and wherein the processor stores a maximum pressure and is configured to trigger an alarm when the pressure sensor measures the maximum pressure.

8. The system of claim 1, wherein the scope device further includes a gyroscope sensor to measure an angular rate of the elongated shaft as it deflects within the target surgical site.

9. The system of claim 1, wherein the scope device further includes a pH sensor.

10. The system of claim 1, wherein the housing is rectangular.

11. The system of claim 10, wherein the window is on a long side of the housing, and wherein a shape of the window is a square.

12. The system of claim 1, wherein the pressure sensor provides the sensor data to the processor by a lead coupled to the pressure sensor and extending through the shaft, and wherein portions of the lead are within the housing.

13. The system of claim 1, wherein the pressure sensor is below the window of the housing and proximate a surface of the shaft.

14. A scope system, comprising:
a processor; and
a single-use scope device, comprising:
 a handle configured to remain outside of a body; and
 an elongated shaft extending from the handle to a distal tip and including a working channel extending therethrough, the working channel being open at the distal tip of the shaft, the shaft being configured to be inserted through a bodily lumen to a target surgical site, the shaft including first and second sensors transmitting to the processor first and second sensor data, respectively;
wherein the first sensor is a pressure sensor embedded in a housing mounted within the distal tip of the shaft, an active portion of the pressure sensor being adjacent to a window of the housing and below a surface of the shaft, the active portion being covered by a water-tight coating that separates the active portion of the pressure sensor from fluid surrounding the scope device while permitting the active portion of the pressure sensor to measure pressure in the fluid surrounding the scope device, the scope device being configured for use in one of ureteroscopy, hysteroscopy, bronchoscopy, or cystoscopy.

15. The system of claim 14, wherein the second sensor is one of a temperature sensor, a pH sensor, a capacitive sensor, or a gyroscope sensor.

16. The system of claim 14, further comprising a fluid source coupled to the scope device, the fluid source providing fluid through the handle and the shaft to the target surgical site.

17. The system of claim 14, wherein the processor includes a display screen and a user interface, the display screen displaying the first and second sensor data to a user.

18. The system of claim 14, wherein the pressure sensor is coupled to a lead that extends through the shaft.

19. The system of claim 14, wherein the housing is rectangular.

* * * * *